United States Patent
Brunel (12)

(10) Patent No.: US 6,447,480 B1
(45) Date of Patent: Sep. 10, 2002

(54) DISPOSABLE INJECTION DEVICE DESIGNED TO BE PRE-FILLED

(75) Inventor: Marc Brunel, Toulouse (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/806,574

(22) PCT Filed: Sep. 30, 1999

(86) PCT No.: PCT/FR99/02325

§ 371 (c)(1),
(2), (4) Date: Apr. 2, 2001

(87) PCT Pub. No.: WO99/20059

PCT Pub. Date: Apr. 13, 2000

(30) Foreign Application Priority Data

Oct. 1, 1998 (FR) .............................. 98 12308

(51) Int. Cl.⁷ .................................. A61N 5/00
(52) U.S. Cl. .................. 604/110; 604/192; 604/263
(58) Field of Search ................ 604/110, 111, 604/187, 196, 198, 267, 218

(56) References Cited

U.S. PATENT DOCUMENTS

| 3,916,893 A | 11/1975 | De Felice .................. 604/193 |
| 4,639,250 A | 1/1987 | Rycroft .................... 604/263 X |
| 5,667,494 A | 9/1997 | Van Den Haak ........ 604/110 X |

FOREIGN PATENT DOCUMENTS

| DE | 847 473 | 8/1952 |
| DE | 1 909 794 | 9/1970 |
| DE | 2 008 751 | 8/1971 |
| EP | 0 111 796 | 6/1984 |
| EP | 0 150 681 | 8/1985 |
| EP | 0 191 508 | 8/1986 |
| EP | 0 588 148 | 3/1994 |
| EP | 0 602 883 | 6/1994 |
| EP | 0 720 857 | 7/1996 |
| FR | 2 208 684 | 6/1974 |
| FR | 2 330 413 | 6/1977 |
| FR | 2 347 055 | 11/1977 |
| FR | 2 412 320 | 7/1979 |
| WO | WO 84/04252 | 11/1984 |
| WO | WO 85/04590 | 10/1985 |

*Primary Examiner*—Anhtuan T. Nguyen
(74) *Attorney, Agent, or Firm*—Young & Thompson (57) ABSTRACT

The invention relates to an injection device comprising a syringe body (1), which delimits a chamber which is designed to be filled with liquid, and a unit (25) for distributing the liquid, comprising an end piece for closing off the said chamber, which is extended by a base, which supports an injection needle which is protected by a protective cap (35), the said distribution unit being mobile axially between a closing-off position of the chamber, and a position for injection of the liquid. According to the invention, the unit (25) for distributing comprises an intermediate section (31) between the base and the closing-off end piece, and the syringe body (1) comprises a ring (6) which delimits two superimposed compartments (18, 19), which can each accommodate the said intermediate section. In addition, the protective cap (35) and this intermediate section (31) have complementary profiles (34, 38) in the form of a cam, which can permit generation of axial displacement of the unit (25) for distributing, towards its injection position, during rotation of the said protective cap.

10 Claims, 5 Drawing Sheets

DISPOSABLE INJECTION DEVICE DESIGNED TO BE PRE-FILLED

The invention relates to an injection device of the single-use type, which is designed to be pre-filled with a dose of liquid, in particular a medicinal liquid, to be injected.

Single-use injection devices which are designed to be pre-filled comprise a syringe body, which is either provided with a base, in which there is sealed a needle, which is protected by a protective cap, or comprise a conical male locking connection, which makes it possible to fit onto the said syringe body a conical female locking connection, which supports an injection needle protected by a protective cap, the said conical connections defining an assembly which is commonly known as a "LÜER conical assembly".

The most conventional injection devices, known as the "wet needle" type, are of the type provided with a syringe body comprising a base, in which there is sealed an injection needle, which is closed off by means of a protective elastomer cap, which is provided with a inner blind bore contained in the base of the said cap, inside which the end of the said needle is forced, such as to guarantee the sealing of the injection device before injection takes place.

The first disadvantage of injection devices of this type consists in the fact that when the protective cap is put into place, the injection needle must be centred perfectly in relation to the bore in the said cap. However, in practice, this centring is sometimes approximate, such that fitting of the cap frequently leads to deterioration of the said cap or needle, resulting in significant numbers of production rejects.

In addition, according to this principle, the quality of the needle (sharpness, silicone coating), is systematically affected by the occurrence of friction of the point of the said needle against the inner wall of the blind bore in the cap, when the latter is forced on.

Finally, the liquid contained in these injection devices is necessarily in contact with the materials which constitute the injection needle and the protective cap, which, for certain types of liquid, can affect the conservation of the latter.

In order to eliminate these disadvantages, numerous injection devices known as the "dry needle" type have been designed, wherein the injection needle is isolated from the liquid contained in the syringe body until the moment of injection.

A first type of "dry needle" injection device is that which is commonly used in dentistry, and comprises a bottle, which contains the liquid to be injected, and is closed off by a membrane, and a double-point needle, which can be displaced axially relative to the said bottle, such as to pierce the membrane at the moment of injection. Injection devices of this type are described in particular in patents DE-847473, FR-2347055, U.S. Pat. No. 4,639,250, EP-602883, DE-2008751, DE-1909794.

This type of injection device has two sorts of disadvantages. In fact, firstly, the fact of needing a double-point needle leads to a increase in the cost price of these injection devices, derived firstly from the cost of the said needle itself, and secondly from the necessity of carrying out two sharpening operations instead of a single sharpening operation required for a conventional needle. In addition, for needles with a small diameter, it often happens that problems of coring arise, leading to the inclusion of particles of membrane inside the aperture of the needle, which either close off this aperture, or are injected together with the liquid.

A second type of "dry needle" injection device comprises a syringe body which accommodates two stoppers, which delimit the chamber containing the liquid, and onto which a base is crimped, the said syringe body additionally having a compartment which is provided with a duct for communication with the injection needle, which is disposed such as to be put into contact with the chamber only after the pistons have been displaced axially.

Injection devices of this type, which are described in particular in patents FR-2412320, FR-2208684, EP-191508, EP-588148 and EP-720857, make it possible to eliminate the disadvantages of the above-described injection devices. However, they themselves also have two disadvantages. In fact, firstly, the operation of crimping the base onto the syringe body is problematic, and requires particular care in order to guarantee perfect sealing between the said base and the said syringe body. In addition, and above all, injection devices of this type can be subject to accidental escape of the liquid contained in the chamber, resulting for example from expansion of the volume of gas contained in the said chamber, or from depressurisation, in particular during transport by air, which lead to axial displacement of the stopper for access to the compartment for discharge of the liquid.

A third type of "dry needle" injection device, described in particular in patents EP-150681, EP-111796, FR-2330413 and WO-8404252, makes it possible to eliminate all of the above-described disadvantages. For this purpose, these injection devices comprise firstly a syringe body, which is provided with a chamber closed off by a rubber stopper, which contains a longitudinal through-bore, and secondly, a base which is mobile axially inside the bore of the said stopper, and is provided with ducts which are disposed such as to put the injection needle and the chamber into communication during axial displacement of the said base, which tends to thrust the latter into the stopper.

The invention relates to an injection device which has a design similar to that of the injection devices of the third type described above, and the main objective of which is to provide an ergonomic injection device, which combines the advantages of these injection devices (sealing, guarantee against risks of accidental escape, etc), the activation of which for the purpose of an injection is carried out very simply, by means of a very natural gesture.

For this purpose, the invention relates to an injection device comprising a syringe body, which delimits a chamber which is designed to be filled with a liquid, in particular a medicinal liquid, and a unit for closing off the chamber and distributing the liquid, comprising an end piece for closing off the said chamber, which is firstly extended by a base, in which there is sealed a needle which is covered by a protective cap, and secondly, which is perforated in the extension of the said needle by a duct for distribution of the liquid, the said unit for closing off and distributing being mobile axially between a position known as the closing-off position, in which the distribution duct is isolated from the chamber of the syringe body, and a position known as the injection position, in which the said distribution duct communicates with the said chamber.

According to the invention, this injection device is characterised in that:

the unit for closing off and distributing comprises an intermediate section, which is disposed between the closing-off end piece and the base, and is placed such as to extend in the extension of the syringe body;

the syringe body comprises a ring which is provided with a front wall, in which there is provided an axial opening for passage of the protective cap, and which delimits two inner compartments which are juxtaposed axially, each of which has a shape which is conjugated with the intermediate section of the unit for closing off and distributing, and can accommodate the said intermediate section, the said compartments being separated by axial stop units which can permit axial displacement of the intermediate section of one compartment towards the other compartment;

the ring and the intermediate section comprise respectively inner and outer conjugated units, for relative locking in rotation of the said ring and intermediate section;

the cap comprises an end section, which is designed to extend through the axial opening of the front wall of the ring, such as to cover the base and abut axially the intermediate section of the unit for closing off and distributing;

the end section of the cap, and the intermediate section of the unit for closing off and distributing have at the front, and opposite, conjugated profiles in the form of a cam, which can give rise to axial displacement of the unit for closing off and distributing, from its closing-off position towards its injection position, during movement of rotation of the protective cap; and the cap comprises outer units which are designed to abut axially the front wall of the ring, in a position in which the said cap covers the base of the unit for closing off and distributing.

The activation of an injection device of this type, for the purpose of the injection, is thus derived from simple rotation of the protective cap, which gives rise to axial displacement of the unit for closing off and distributing, which brings the needle and the chamber of the syringe body into communication.

This activation thus simply requires performance of a natural movement, which is carried out conventionally, in order to remove a protective cap, consisting of imparting movement of rotation to the said protective cap.

In addition, the axial displacement of the unit for closing off and distributing which is generated by this rotation of the protective cap is irreversible, owing to the fact that any further, inverse displacement, is subsequently prevented.

According to another characteristic of the invention, each profile in the form of a cam has two slopes, which extend symmetrically on both sides of a longitudinal axis of symmetry, such as to permit rotation of the protective cap in either direction of rotation.

Thus, the activation of the injection device can be obtained equally well by turning the protective cap in either direction of rotation.

According to another characteristic of the invention, the profiles in the form of a cam, of the intermediate section of the unit for closing off and distributing, and of the end section of the protective cap, have respectively a conjugated concave shape and a convex shape.

According to another characteristic of the invention, the end section of the protective cap comprises a radial outer pin at the level of at least one of the profiles in the form of a cam.

In addition, for each outer pin of the protective cap, the ring then comprises a cutout provided in the periphery of the axial opening of the front wall, the said cutout being provided such as to be offset angularly by an angle ($\alpha$) relative to the outer pin, in the closing-off position of the unit for closing off and distributing, and to be plumb with the said outer pin in the injection position of the said unit for closing off and distributing.

According to this arrangement, the protective cap cannot be removed without firstly having undergone a movement of rotation, which makes it possible to bring each outer pin plumb with a cutout provided in the front wall of the ring, during which movement of rotation, as previously stated, the unit for closing off and distributing is automatically displaced axially.

The movement to be imparted to the protective cap in order to remove the latter thus corresponds exactly to the conventional movement imparted to any protective cap in order to remove it, i.e. a movement of rotation, combined with a traction force exerted on the said protective cap.

According to another characteristic of the invention, for each cutout in the front wall of the ring, the protective cap comprises a longitudinal fin, which is offset angularly by an angle ($\alpha$) relative to each outer pin of the said protective cap, which can slide in the said cutout when this protective cap is presented opposite the interior of the ring.

The presence of this (or these) fin(s) makes it possible to assemble the unit for closing off and distributing/and the protective cap/in a preceding step, then to fit the assembly by introducing it inside the ring, during which assembly the angular position of each outer pin of the cap is automatically indexed by means of the arrangement of the said fin(s).

In addition, and preferably, each longitudinal fin of the protective cap is interrupted at a distance from the end of the end section of the said protective cap, and has a thickness which is designed to abut axially the front wall of the ring.

In addition, according to another characteristic of the invention, each fin of the protective cap comprises a lateral outer surface which is inclined longitudinally, such as to form a ramp, which can allow the said fin to clear the cutout in the front wall of the ring, on completion of introduction of the said protective cap inside the said ring.

This form of the fins makes it possible to fit the closing-off and distributing unit/protective cap assembly inside the ring as previously described, whilst imparting to the said fins the function of an axial stop for the said protective cap on the front wall of the ring, once this assembly has been completed.

According to another characteristic of the invention:

the ring of the syringe body delimits an inner receptacle which has a cylindrical shape, and comprises at least one longitudinal inner groove, relative to the base of which there projects a catch, provided in an intermediate position along the said groove, which catch has longitudinally an outer surface in the form of a dihedron, which can act as an axial stop unit separating the two inner compartments of the said ring;

for each groove in the ring, the intermediate section of the unit for closing off and distributing comprises a lateral lug, which can be accommodated in the said groove, and has a shape which is conjugated with the compartments delimited by the catch which extends in the latter.

Additionally, the injection device according to the invention advantageously comprises a closing-off stopper with dimensions which are suitable for being inserted in the syringe body, provided with a through bore which opens into the said syringe body at a countersink.

In addition, in this case, the unit for closing off and distributing has dimensions which are designed to be inserted in the bore in the closing-off stopper, and comprises a distribution duct containing a transverse branch, which is disposed such as to be positioned recessed from the countersink in the said closing-off stopper, in the closing-off position of the unit for closing off and distributing, and to extend into the said countersink, in the injection position of the said unit.

Other characteristics, objects and advantages of the invention will become apparent from the following detailed description provided with reference to the attached drawings, which represent a preferred embodiment, by way of non-limiting example. In these drawings.

Figure 1:
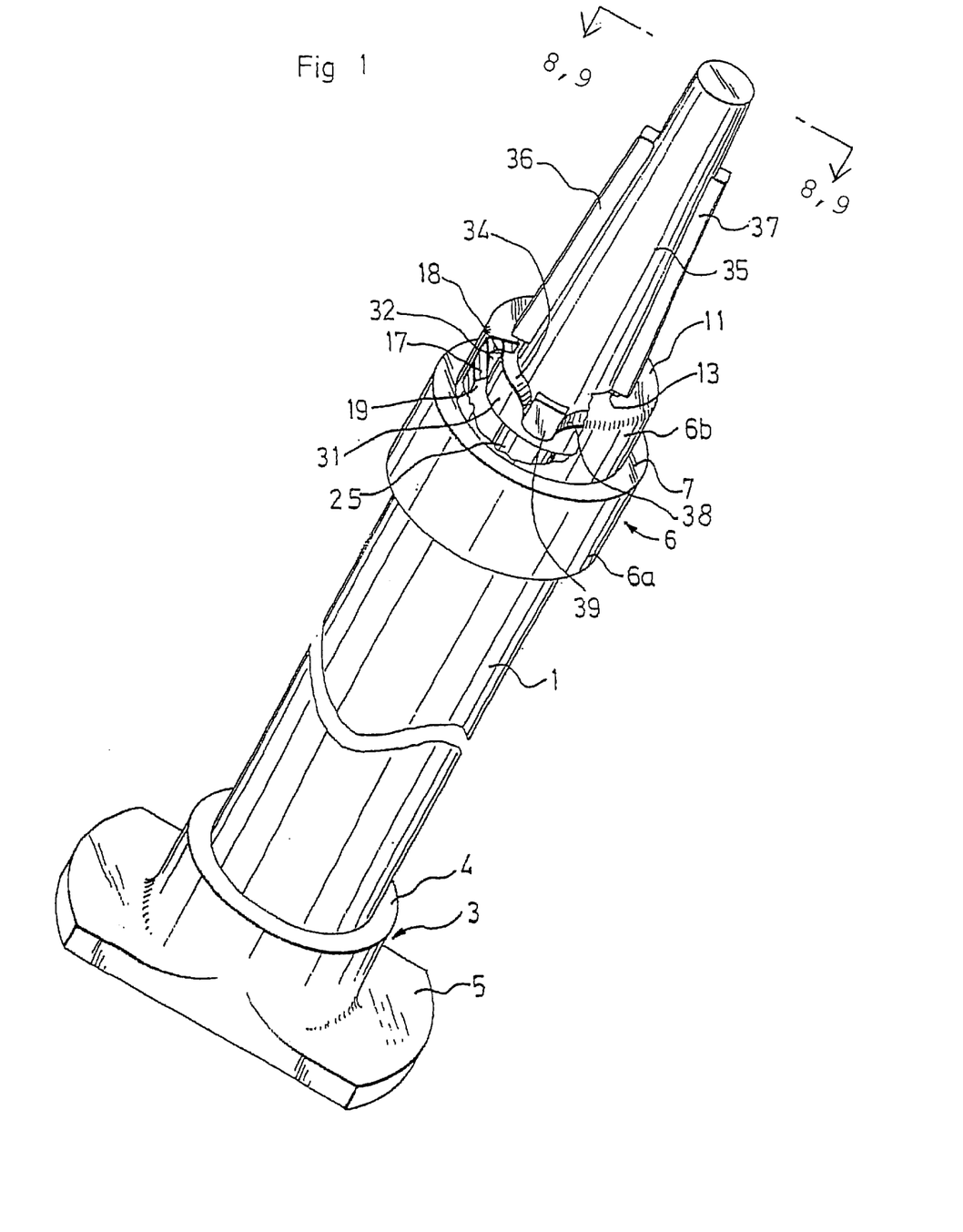
FIG. 1 is a partially cutout perspective view of an injection device according to the invention.

The injection device represented in FIG. 1 is of the single-use type, i.e. it is designed to be filled with a liquid to be injected. It should be noted that although the injection device as represented does not have a protective case, which is designed to make it possible to protect the needle, whilst avoiding any risks of being pricked, after injection has taken place it can be equipped in a known manner with any protective case of a conventional type which fulfils this function.

This injection device comprises firstly a conventional syringe body, containing a cylindrical tube 1, which is provided with an outer collar 2 at one of its ends.

This syringe body additionally comprises an end piece 3, which is designed to be fitted in a conventional manner onto the end section of the cylindrical tube 1, opposite the collar 2, and in a conventional manner comprises a sleeve 4, which is designed to be fitted onto the said end, and two fins 5, to be gripped by the fingers.

The injection device additionally comprises a ring 6, which is designed to cover the end section of the cylindrical tube 1, opposite the end piece 3.

Figure 2:
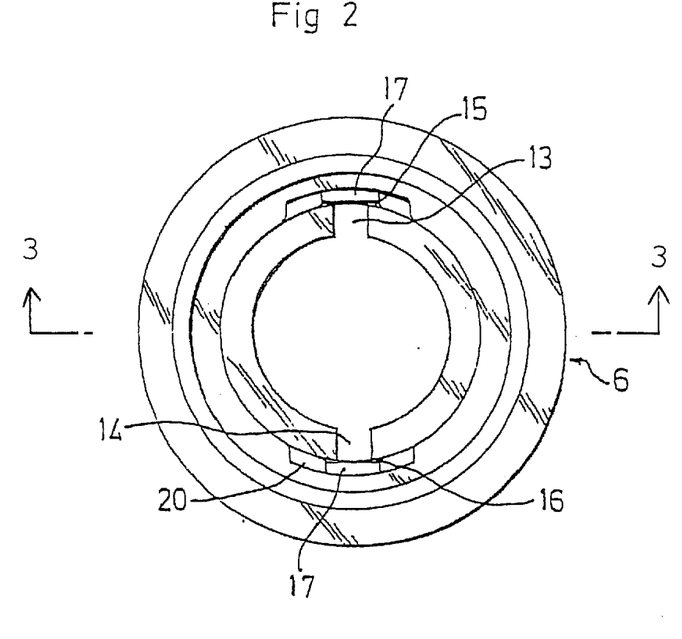
FIG. 2 is a front view from beneath of the ring of the syringe body of this injection device.
Figure 3:
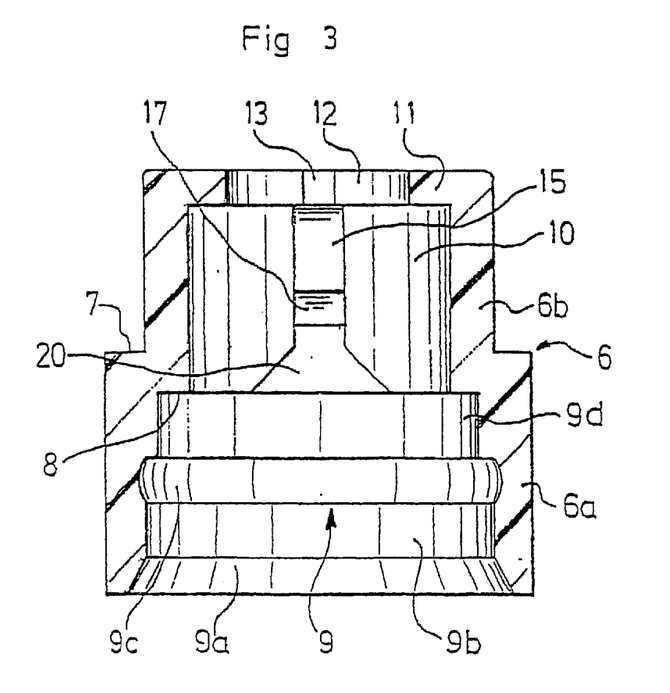
FIG. 3 is a longitudinal cross-section, through an axial plane 3 of this ring.

This ring 6 consists longitudinally of two cylindrical sleeves 6a, 6b, with different outer and inner diameters, which are separated by respective outer 7 and inner 8 shoulders.

The first sleeve 6a, which has the larger diameter, is designed to be fitted along its longer length onto the end section of the cylindrical tube 1 of the syringe body. On the interior, this sleeve 6a has a bore 9 which is divided longitudinally into four sections, which consist in succession of:

a first end section 9a, which is designed to be presented opposite the end of the syringe body during fitting of the ring 6, and has a frusto-conical shape defining a ramp, which can facilitate this fitting;

a first intermediate section 9b, which has a cylindrical shape with an inner diameter which is conjugated with the outer diameter of the cylindrical tube 1;

a second intermediate section 9c, with a toric shape, which is designed to be clipped onto the collar 2 of the cylindrical tube 1; and a fourth section 9d, for joining with the second sleeve 6b, with a cylindrical shape which has an inner diameter slightly smaller than that of the first intermediate section 9b.

The second sleeve 6b, which has smaller dimensions, has in its interior a cylindrical bore 10, which, as previously stated, is separated from the joining section 9d of the first sleeve 6a by the inner shoulder 8.

Opposite the first sleeve 6a, this second sleeve 6b is closed off by a front wall 11, which is provided with an axial circular opening 12 with a diameter smaller than that of the bore 10.

This front wall 11 comprises two diametrically opposite cutouts 13, 14, which are provided in the periphery of the axial opening 11, and define together with the latter a straight slot for indexing of the orientation of the protective cap during fitting of the injection device.

In addition, the second sleeve 6b also has two diametrically opposite longitudinal inner grooves 15, 16, which each extend plumb in relation to a cutout 13, 14.

Each of these grooves 15, 16, which has a width which is constant along its longer length, additionally has an end section 20 for joining with the bore 9 of the first sleeve 6a, with a width which increases, such as to form an intake funnel.

Finally, this second sleeve 6b comprises a catch such as 17, with a triangular longitudinal section which projects relative to the base of each of these grooves 15, 16.

Figure 8:
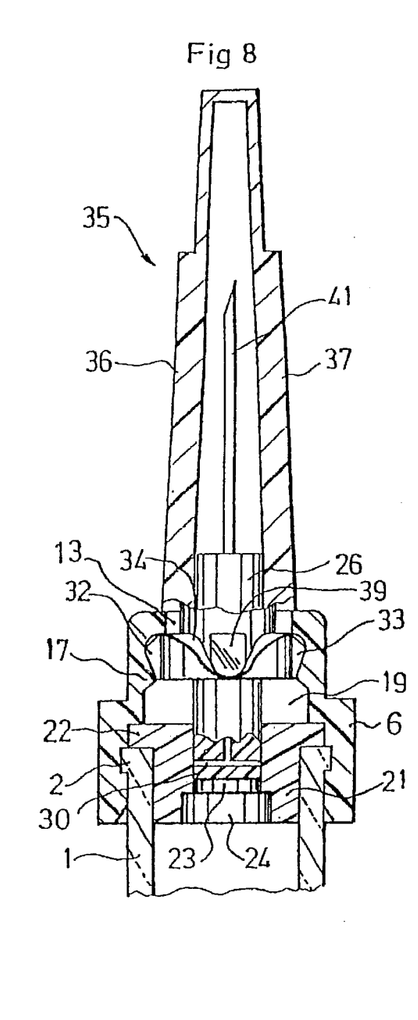
FIGS. 8 and 9 are longitudinal views of the interior of this injection device, respectively in its closing-off position and in its injection position, before removal of the protective cap, in which the unit for closing off and distributing and the said protective cap are represented partially in cross-section, through an axial plane 8, 9.
Figure 9:
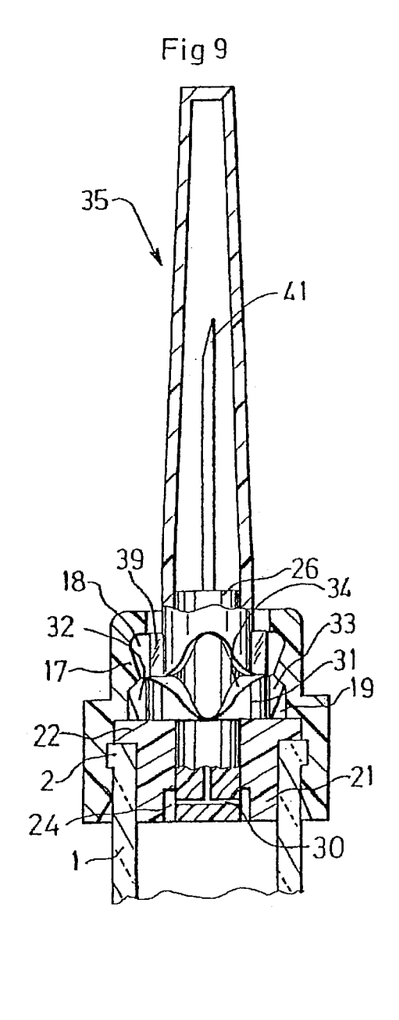
Figure 10:
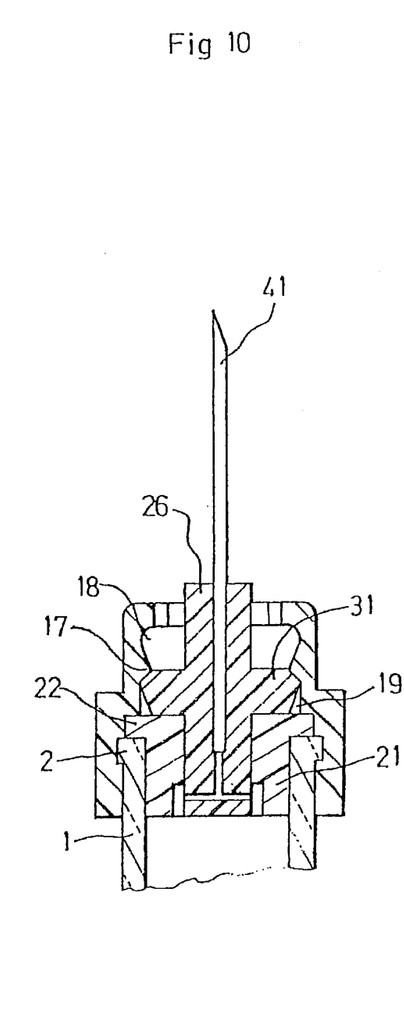
FIG. 10 is a longitudinal cross-section, through the axial plane 8, 9 of this injection device, in its injection position, after the protective cap has been removed.

As shown in FIGS. 8 to 10, if the ring 6 is considered in cross-section through an axial longitudinal plane which intersects the said ring at the grooves 15, 16, the second sleeve 6b is thus divided in its interior into two chambers 18, 19, which are juxtaposed longitudinally, and are separated from one another by the catches 17.

In addition, the injection device comprises means for closing off the end of the cylindrical tube 1 of the syringe body, opposite the end piece 3, which can permit injection of the liquid contained in the said tube.

These means for closing off comprise firstly a cylindrical stopper 21, which can be inserted in the cylindrical tube 1, and is provided with a cylindrical stop collar 22 on the end of the said tube.

This stopper 21 is additionally provided with a through cylindrical bore 23, which opens into a countersink 24 provided in the front surface of the said stopper, opposite the collar 22.

Figure 4:
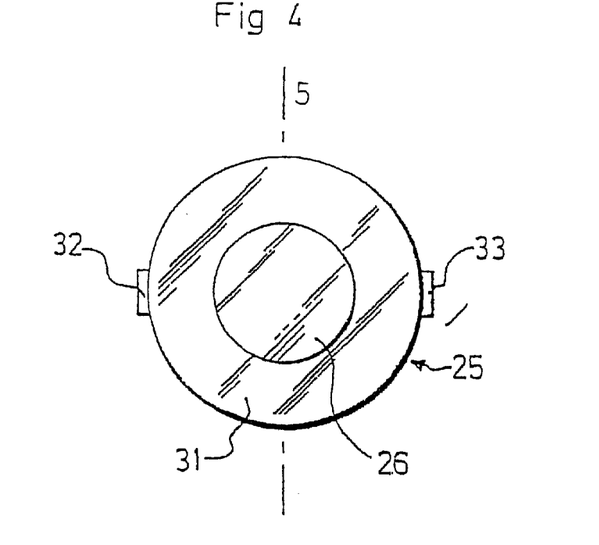
FIG. 4 is a front view from beneath of the unit for closing off and distributing of this injection device.
Figure 5:
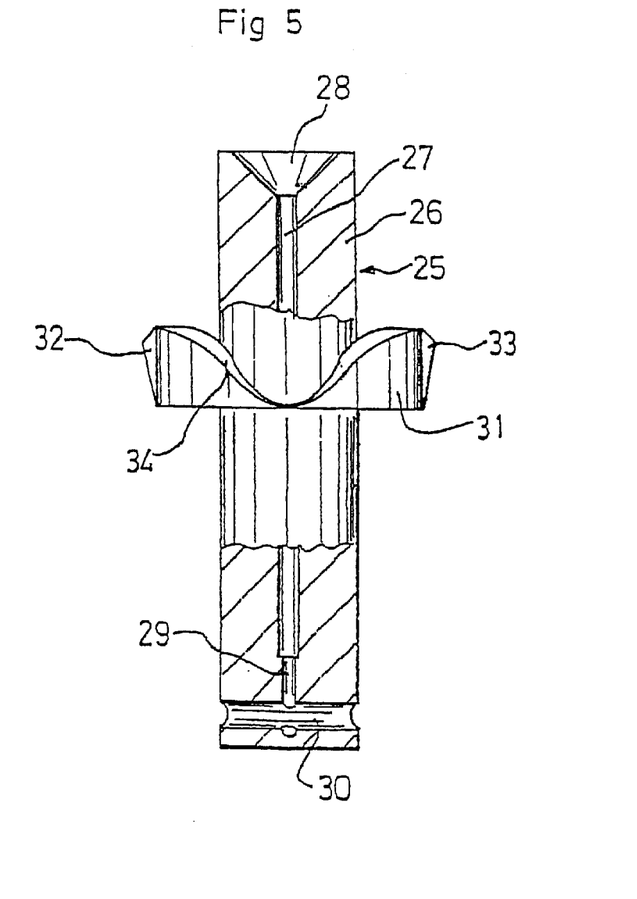
FIG. 5 is a longitudinal view partially in cross-section, through an axial plane 5 of this unit for closing off and distributing.

These means for closing off additionally comprise a unit 25 for closing off and distributing, which is in the form of a cylindrical shaft with an outer diameter which is designed to be accommodated in the bore 23 in the stopper 21.

This shaft 26 is also provided along its longer length with a longitudinal axial bore 27 which opens into a countersunk hole 28 provided in one of the front surfaces of the said shaft, the said bore being designed in a conventional manner to receive an injection needle 41.

This shaft 26 is also provided in the extension of the bore 27 with an axial duct 29 for connection of the said bore with a through transverse bore 30, which is provided at a short distance from the front surface of the said shaft, opposite that in which the countersunk hole 28 is provided.

This unit 25 for closing off and distributing additionally comprises an intermediate flange 31, which consists of a disc which has a generally cylindrical shape, and a diameter conjugated with that of the inner diameter of the bore 10 in the second sleeve 6b of the ring 6.

This intermediate flange 31, which is designed to be able to be accommodated in one or the other chamber 18, 19 of the ring 6, and to be able to be displaced axially in both directions of one of the said chambers towards the other, has for this purpose two diametrically opposite lugs 32, 33, with a substantially triangular longitudinal cross-section, which is conjugated with that of the cross-sections of the grooves 15, 16 which form these chambers 18, 19, and are delimited by the catches 17.

Finally, this intermediate flange 31 comprises an upper front surface in which there are provided two recesses such as 34, which have a concave shape with a longitudinal axis of symmetry, each of the said recesses being disposed such that the said axis of symmetry is offset by an angle a equivalent to 90°, relative to the lugs 32, 33.

Figure 6:
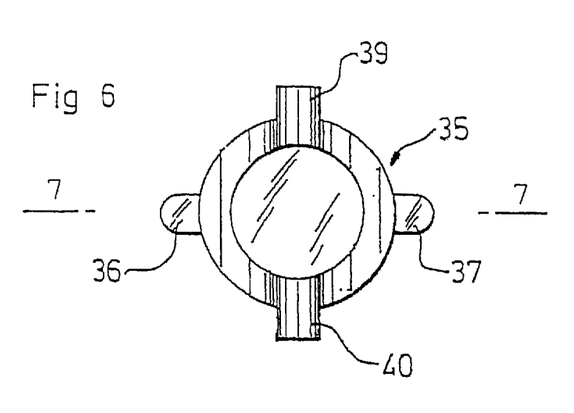
FIG. 6 is a front view from beneath of the protective cap of this injection device.
Figure 7:
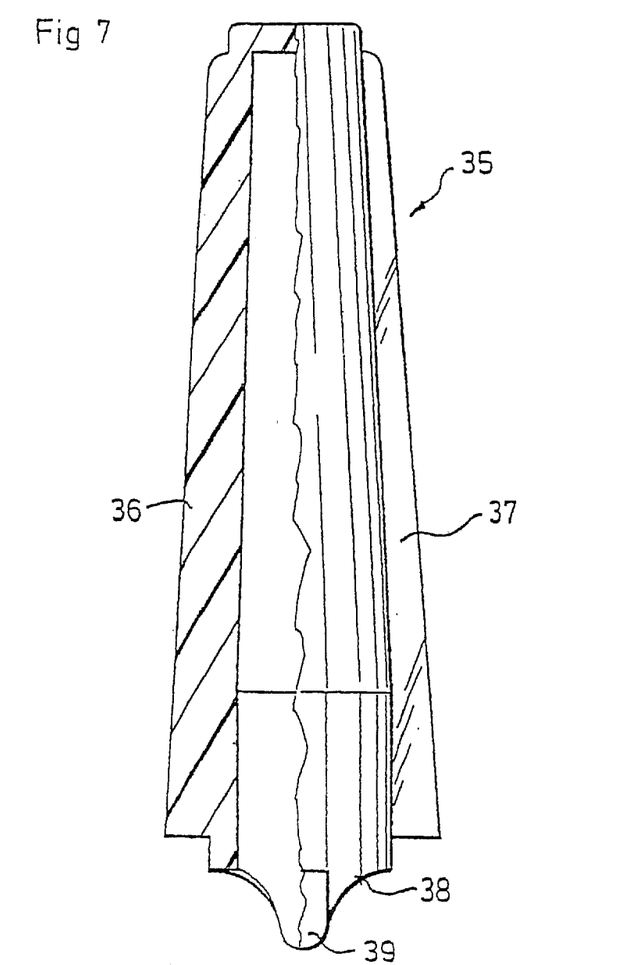
FIG. 7 is a longitudinal view partially in cross-section, through an axial plane 7, of this protective cap.

Finally, the injection device comprises a protective cap 35, which is designed to cover the injection needle 41.

This protective cap has a generally frusto-conical shape, with a basic diameter which is designed to be able to extend through the axial opening 12 provided in the front wall 11 of the ring 6.

This protective cap 35 additionally comprises two diametrically opposite longitudinal fins 36, 37, which define a maximum overall diameter of the said cap, along the axis of the said fins, which is slightly greater than the diameter which separates the base of the cutouts 13, 14 provided in the front wall of the ring 6.

These fins 36, 37 are also interrupted at a distance from the open lower end of the protective cap 35, such that, as shown in FIG. 8, they abut axially the front wall 11 of the ring 6, when the injection device has been assembled.

In the extension of its open end, this protective cap 35 also comprises two diametrically opposed ears such as 38, in the form of a convex undulation which is complementary to the concave profiles of the recesses 34 in the intermediate flange 31 of the unit 25 for closing off and distributing.

In addition, at each ear 38, this protective cap 35 comprises an outer radial pin 39, 40.

The operations for assembly of this injection device are described hereinafter.

Firstly, the protective cap 35 is assembled with the unit 25 for closing off and distributing, such as to make the respective concave and convex profiles of the recesses 34 and the ears 38 co-operate and fit together.

Finally, the above-described assembly is introduced inside the ring 6, the relative positioning in rotation of the said ring and the said assembly being indexed by means of the fins 36, 37, which are made to slide in the cutouts 13, 14.

This introduction leads firstly to positioning of the fins 36, 37 such that they extend fully outside the ring 6, in the extension of the front wall 11 of the latter, and secondly to positioning of the intermediate flange 31 in the upper chamber 18 of the ring 6.

The stopper 21 is then also put into place in the ring 6, in a position in which the collar 22 of the said stopper is accommodated in the fourth section 9d of the first sleeve 6a of the ring 6.

In this position of the stopper 21, and as shown in FIG. 8, the transverse duct 30 of the shaft 26 of the unit 25 for closing off and distributing is positioned in the bore 23 of the said stopper, recessed relative to the countersink 24 of the latter. In addition, this stopper 21 closes off at the front the lower compartment 19 of the ring 6, such as to limit the axial displacement downwards of the unit 25 for closing off and distributing.

Finally, the last operation consists of presenting the syringe body opposite the above-described pre-assembled elements, and of fitting the said syringe body inside the ring 6, until the collar 2 of the cylindrical tube 1 clips into the toric intermediate section 9c of the first sleeve 6a of the said ring.

When this assembly has been carried out, the protective cap 35 can no longer be thrust inside the ring, owing to the arrangement of the fins 36, 37, which are positioned such as to abut the front wall 11 of the said ring. In addition, this protective cap 35 cannot be removed, without previously having undergone a movement of rotation, owing to the presence of the radial pins 39, 40.

Consequently, after the syringe body has been filled, and the latter has been closed off by a piston body of the conventional type, the injection device can then be handled, stored etc., without any risk of escape of liquid, or of contamination of this liquid.

Finally, for the purpose of an injection, and as shown in FIG. 9, it is sufficient for the user to turn the protective cap 35 by a quarter turn in either direction, and to pull the latter such as to separate it from the syringe body.

During this removal, and firstly, the unit 25 for closing off and distributing is automatically displaced axially towards an injection position, in which, firstly, the intermediate flange 31 is accommodated in the lower chamber 19 of the ring 6, and secondly, the transverse duct 30 opens into the countersink 24 in the stopper 21, thus permitting escape and injection of the liquid.

In addition, the radial pins 39, 40 of the protective cap 35 are automatically brought plumb with the cutouts 13, 14 in the ring 6, thus permitting efficient removal of the said protective cap.

What is claimed is:

1. An injection device comprising a syringe body (1, 3, 21), which delimits a chamber which is designed to be filled with a liquid, in particular a medicinal liquid, and a unit (25) for closing off the chamber and distributing the liquid, comprising an end piece for closing off the said chamber, which is firstly extended by a base, in which there is sealed a needle (41) which is covered by a protective cap (35), and secondly, which is perforated in the extension of the said needle by a duct (29, 30) for distribution of the liquid, the said unit (25) for closing off and distributing being mobile axially between a position known as the closing-off position, in which the distribution duct (29, 30) is isolated from the chamber of the syringe body (1, 3, 21), and a position known as the injection position, in which the said distribution duct communicates with the said chamber, wherein, in the said injection device:

the unit (25) for closing off and distributing comprises an intermediate section (31), which is disposed between the closing-off end piece and the base, and is placed such as to extend in the extension of the syringe body (1, 3, 21);

the syringe body (1, 3, 21) comprises a ring (6) which is provided with a front wall (11), in which there is provided an axial opening (12) for passage of the protective cap (35), and which delimits two inner compartments (18, 19) which are juxtaposed axially, each of which has a shape which is conjugated with the intermediate section (31) of the unit (25) for closing off and distributing, and can accommodate the said intermediate section, the said compartments being separated by axial stop units (17) which can permit axial displacement of the intermediate section (31) of one compartment (18,19) towards the other compartment (19, 18);

the ring (6) and the intermediate (31) section comprise respectively inner and outer conjugated units (15, 16, 32, 33), for relative locking in rotation of the said ring and intermediate section;

the protective cap (35) comprises an end section, which is designed to extend through the axial opening (12) in the front wall (11) of the ring (6), such as to cover the base and abut axially the intermediate section (31) of the unit for closing off and distributing (25);

the end section of the protective cap (35), and the intermediate section (31) of the unit (25) for closing off and distributing have at the front, and opposite, conjugated profiles (34, 38) in the form of a cam, which can give rise to axial displacement of the unit (25) for closing off and distributing, from its closing-off position towards its injection position, during movement of rotation of the protective cap (35); and the protective cap (35) comprises outer units (36, 37) which are designed to abut axially the front wall (11) of the ring (6), in a position in which the said cap covers the base of the unit (25) for closing off and distributing.

2. An injection device as claimed in claim 1, wherein the profiles in the form of a cam (34, 38), of the intermediate section (31) of the unit (25) for closing off and distributing, and of the end section of the protective cap (35), have respectively a conjugated concave shape and a convex shape.

3. An injection device as claimed in claim 1, wherein:

the end section of the protective cap (35) comprises a radial outer pin (39, 40) at the level of at least one of the profiles (38) in the form of a cam; and for each outer pin (39, 40) of the protective cap (35), the ring (6) comprises a cutout (13, 14) which is provided in the periphery of the axial opening (12) of the front wall (11), the said cutout being such as to be offset angularly by an angle ($\alpha$) relative to the outer pin (39, 40), in the closing-off position of the unit (25) for closing off and distributing, and to be plumb with the said outer pin in the injection position of the said unit for closing off and distributing.

4. An injection device as claimed in claim 3, wherein each profile (34, 38) in the form of a cam has two slopes, which extend symmetrically on both sides of a longitudinal axis of symmetry, such as to permit rotation of the protective cap (35) in either direction of rotation.

5. An injection device as claimed in claim 3, wherein the angle ($\alpha$) is substantially equivalent to 90°.

6. An injection device as claimed in claim 3, wherein for each cutout (13, 14) in the front wall (11) of the ring (6), the protective cap (35) comprises a longitudinal fin (36, 37), which is offset angularly by an angle ($\alpha$) relative to each outer pin (39, 40) of the said protective cap, which can slide in the said cutout when this protective cap (35) is presented opposite the interior of the ring (6).

7. An injection device as claimed in claim 6, wherein each longitudinal fin (36, 37) of the protective cap (35) is interrupted at a distance from the end of the end section of the said protective cap, and has a thickness which is designed to abut axially the front wall (11) of the ring (6).

8. An injection device as claimed in claim 7, wherein each fin (36, 37) of the protective cap (35) comprises a lateral outer surface which is inclined longitudinally, such as to form a ramp, which can allow the said fin to clear the cutout (13, 14) in the front wall (11) of the ring (6), on completion of introduction of the said protective cap inside the said ring.

9. An injection device as claimed in claim 1, wherein:

the ring (6) of the syringe body (1, 3, 21) delimits an inner receptacle which has a cylindrical shape, and comprises at least one longitudinal inner groove (15, 16), relative to the base of which there projects a catch (17), provided in an intermediate position along the said groove, which catch has longitudinally an outer surface in the form of a dihedron, which can act as an axial stop unit separating the two inner compartments (18, 19) of the said ring;

for each groove (15, 16) in the ring (6), the intermediate section (31) of the unit (25) for closing off and distributing comprises a lateral lug (32, 33), which can be accommodated in the said groove, and has a shape which is conjugated with the compartments (18, 19) delimited by the catch (17) which extends in the latter.

10. A device as claimed in claim 1, wherein it comprises:

a closing-off stopper (21) with dimensions which are suitable for being inserted in the syringe body (1, 3), provided with a through bore (23) which opens into the said syringe body at a countersink (24); and the unit (25) for closing off and distributing has dimensions which are designed to be inserted in the bore (23) in the closing-off stopper (21), and comprises a distribution duct (29, 30) containing a transverse branch (30), which is disposed such as to be positioned recessed from the countersink (24) in the said closing-off stopper, in the closing-off position of the unit (25) for closing off and distributing, and to extend into the said countersink, in the injection position of the said unit.

* * * * *

UNITED STATES PATENT AND TRADEMARK OFFICE
CERTIFICATE OF CORRECTION

| | | |
|---|---|---|
| PATENT NO. | : 6,447,480 B1 | Page 1 of 1 |
| DATED | : September 10, 2002 | |
| INVENTOR(S) | : Marc Brunel | |

It is certified that error appears in the above-identified patent and that said Letters Patent is hereby corrected as shown below:

<u>Title page,</u>
Amend item [87] PCT Publication No. as follows:
-- [73]   PCT Pub. No.:   WO 00/20059 --.

Signed and Sealed this

Twenty-fourth Day of December, 2002

JAMES E. ROGAN
*Director of the United States Patent and Trademark Office*